United States Patent [19]

Wright et al.

[11] 3,972,911

[45] Aug. 3, 1976

[54] N,N'(CYANO-PHENYLENE)DIOXAMIC ACIDS AND ESTERS

[75] Inventors: John B. Wright; Charles M. Hall, both of Kalamazoo, Mich.

[73] Assignee: The Upjohn Company, Kalamazoo, Mich.

[22] Filed: June 10, 1974

[21] Appl. No.: 477,816

Related U.S. Application Data

[63] Continuation-in-part of Ser. No. 382,762, July 26, 1973, which is a continuation-in-part of Ser. No. 317,005, Dec. 20, 1972, abandoned.

[52] U.S. Cl. .................. 260/465 D; 260/293.75; 260/293.77; 260/326.2; 260/471 A; 260/471 R; 260/501.11; 260/501.15; 260/518 A; 260/518 R; 260/519; 424/304; 424/267; 424/274; 424/309; 424/316; 424/319
[51] Int. Cl.² ............................... C07C 121/78
[58] Field of Search .......................... 260/465 D

[56] References Cited
UNITED STATES PATENTS
3,852,324  12/1974  Wright ..................... 260/465 D

*Primary Examiner*—Lewis Gotts
*Assistant Examiner*—Dolph H. Torrence
*Attorney, Agent, or Firm*—Martin B. Barancik; Roman Saliwanchik

[57] ABSTRACT

It has now been discovered that novel compounds of FIG. 1

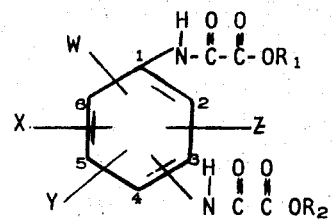

are useful in the prophylactic treatment of sensitized humans and animals for allergy and all anaphylactic reactions of a reagin or non-reagin mediated nature. Additionally, these compounds are intermediates to the acids and physiologically acceptable salts which also have the same biological utility. The compounds of the invention are formulated with pharmaceutical carriers for oral, parenteral, inhalation or rectal means of administration.

17 Claims, No Drawings

N,N'(CYANO-PHENYLENE)DIOXAMIC ACIDS AND ESTERS

CROSS REFERENCE TO RELATED APPLICATION

This application is a continuation-in-part of copending U.S. application Ser. No. 382,762, filed July 26, 1973, which is a continuation-in-part of copending U.S. application Ser. No. 317,005, filed Dec. 20, 1972 and now abandoned.

BRIEF SUMMARY OF THE INVENTION

It has now been discovered that novel compounds of FIG. I are useful in the prophylactic treatment of sensitized humans and animals for allergy and all anaphylactic reactions of a reagin or non-reagin mediated nature. Additionally, these compounds are intermediates to the acids and physiologically acceptable salts which also have the same biological utility. The compounds of the invention are formulated with pharmaceutical carriers for oral, parenteral, inhalation or rectal means of administration.

DETAILED DESCRIPTION OF THE INVENTION

In accordance with this invention, there are provided compounds represented by FIG. I, and hereafter referred to as Group I

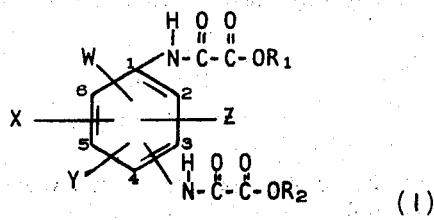

(I)

wherein W, X, Y and Z are the same or different and are selected from the group consisting of hydrogen, alkyl from one to six carbon atoms, inclusive, phenyl, alkoxy with the alkyl group having from one to six carbon atoms, inclusive, hydroxy, nitro, halogen, trifluoromethyl, cyano, with the proviso that cyano is meta to both

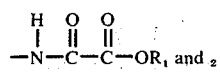

groups, and

wherein Q is selected from

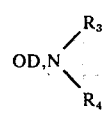

and

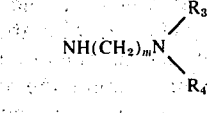

wherein D is selected from the group consisting of hydrogen, alkyl from one to six carbon atoms, inclusive, phenyl,

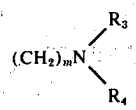

and a physiologically acceptable metal or amine cation; m is 2 or 3, $R_3$ and $R_4$ are the same or different and are selected from the group consisting of hydrogen alkyl from one to three carbon atoms, inclusive, and $R_3$ and $R_4$ when taken together with the nitrogen atom to which they are attached, form a saturated heterocyclic of four to six ring carbon atoms; the

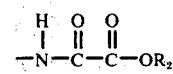

group is located at the 3 or 4 position;

$R_1$ and $R_2$ are the same or different and are selected from the group consisting of hydrogen; a physiologically acceptable metal or amine cation; alkyl of one to 12 carbon atoms, inclusive; cycloalkyl of four to eight carbon atoms, inclusive;

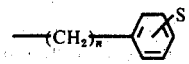

wherein $n$ is an integer of zero to four, inclusive, and S is selected from the group consisting of hydrogen, alkyl of one to six carbon atoms, inclusive, phenyl, halogen, trifluoromethyl, hydroxy, alkoxy of one to four carbon atoms, inclusive, amino, nitro, carboxy, cyano and

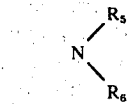

wherein $R_5$ and $R_6$ are the same or different and are selected from the group consisting of hydrogen and alkyl of one to four carbon atoms, inclusive; and

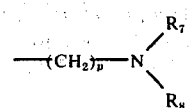

wherein $p$ is an integer of two to four, inclusive, and $R_7$ and $R_8$ are the same or different and are selected from the group consisting of hydrogen and alkyl of one to four carbon atoms, inclusive, and when $R_7$ and $R_8$ are taken together with nitrogen atom to which they are attached form a saturated heterocyclic of three to six ring carbon atoms, inclusive; with the proviso that when one of $R_1$ and $R_2$ is hydrogen or a physiologically acceptable metal or amine cation, the other variable is not hydrogen or a physiologically acceptable metal or amine cation; with the further proviso that when one of W, X, Y and Z is cyano, neither $R_1$ nor $R_2$ is alkyl of one to six carbon atoms, inclusive, phenyl, or

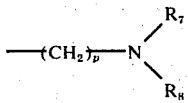

as defined above;
with the further additional overall provisos that
a. one of W, X, Y and Z must be other than hydrogen;
b. when

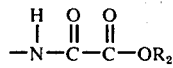

is at the 4 position,
1. and W, X, and Y are hydrogen, then Z may not be alkyl, alkoxy, or halogen, as defined above;
2. no combination of W, X, Y and Z can be alkyl, alkoxy, or halogen, as defined above,
and
c. when

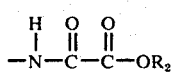

is at the 3 position, and W, X, and Y are hydrogen, then Z may not be at the 4 position when Z is selected from the group consisting of alkyl, alkoxy and halogen, as defined above.

The overall provisos are intended to remove compounds of U.S. Pat. No. 3,639,249 from the scope of the present claims. These provisos apply to each group of compounds and each generic claim.

A further group of compounds are those compounds of Group I wherein W is hydrogen.

A still further group of compounds are those compounds of Group I wherein W and X are hydrogen.

Another group of compounds are those of Group I wherein W, X and Y are hydrogen.

A further group of compounds, hereinafter referred to as Group II are compounds where W is hydrogen, X Y and Z are the same or different and are selected from the group consisting of hydrogen, alkyl of one to four carbon atoms, inclusive, alkoxy of one to four carbon atoms, inclusive, phenyl, hydroxy, nitro, halogen, trifluoromethyl, cyano, with the proviso that cyano is meta to both

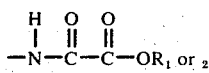

groups, and

where Q is as previously defined in Group I, with the proviso that when D is alkyl, the upper carbon atom limitation is three,

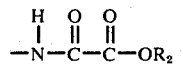

is at the 3 or 4 position; $R_1$ and $R_2$ are as defined in Group I.

Another group of compounds are compounds where W and X are hydrogen, Y and Z are as defined in Group II,

is at the 3 or 4 position, and $R_1$ and $R_2$ are defined as in Group II.

A further group of compounds are where W, X, and Y are hydrogen and Z is as defined in Group II.

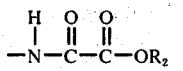

is at the 3 or 4 position, and $R_1$ and $R_2$ are defined as in Group II.

A further group of compounds, hereafter referred to as Group III, are compounds where W and X are hydrogen, Y and Z are the same or different and are selected from the group consisting of hydrogen, alkyl from one to four carbon atoms, inclusive, alkoxy from one to four carbon atoms, inclusive, phenyl, nitro, fluoro, chloro, trifluoromethyl, cyano, with the proviso that cyano is meta to both

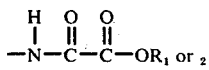

groups and

where Q is as defined in Group I.

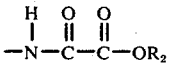

is at position 3 or 4. $R_1$ and $R_2$ are the same or different and are selected from the group consisting of alkyl of one to six carbon atoms, inclusive; cycloalkyl of four to seven carbon atoms, inclusive;

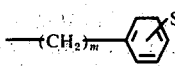

wherein n is an integer from zero to four and S is selected from the group consisting of hydrogen, alkyl of one to four carbon atoms, inclusive, halogen, carboxy, and cyano.

A further group of compounds are where W, X and Y are hydrogen and Z is defined as in Group III.

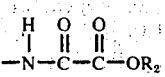

is at the 3 or 4 position. $R_1$ and $R_2$ are as defined in Group III.

A still further group of compounds, hereafter referred to as Group IV, are compounds wherein W and X are hydrogen, Y and Z are defined as in Group III.

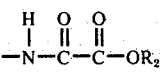

is at the 3 position. $R_1$ and $R_2$ are defined as in Group III.

A further group of compounds are where W, X and Y are hydrogen, and Z, the position of

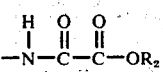

and $R_1$ and $R_2$ are defined as in Group IV.

A still further group of compounds, hereafter referred to as Group V, are compounds wherein W and X are hydrogen, Y and Z are as defined in Group IV with the proviso that Y and Z are at the two or five position and

is limited to

D defined as in Group IV.

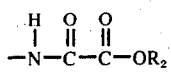

is at the 3 position. $R_1$ and $R_2$ are the same or different and are selected from the group consisting of alkyl of one to six carbon atoms, inclusive, cycloalkyl of five to six carbon atoms, inclusive,

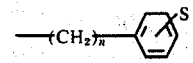

wherein n is zero, one or two and S is selected from the group consisting of hydrogen and ortho or meta alkyl of one to four carbon atoms, inclusive, alkoxy of one to four carbon atoms, inclusive, fluoro, chloro, bromo, carboxy, and cyano.

A further group of compounds are where W, X, and Y are hydrogen; Z, the position of

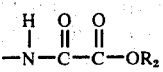

and $R_1$ and $R_2$ are as defined in Group V.

Preferred groups of $R_1$ and $R_2$ are Group I, II, III, IV, V, and sub-groups above wherein $R_1$ is the same as $R_2$. It should be noted that when $R_1$ and $R_2$ are the same, neither $R_1$ nor $R_2$ can be hydrogen or a physiologically acceptable metal or amine cation.

Most preferred compounds are the symmetrical esters of the following phenylene-1,3-dioxamates: 2-chloro-5-cyano; 2-chloro-5-trifluoromethyl; 2-chloro-5-acetyl; 5-cyano; 5-nitro; 5-carboxy. Most preferred esters of these compounds are the dibenzyl and diphenethyl. Activity time spans can be increased significantly when using these preferred esters.

As employed in the above disclosure and throughout the specification, the term "halogen" includes fluoro, chloro, bromo, and iodo. The phrase "alkyl of one to six carbon atoms, inclusive" includes methyl, ethyl, propyl, butyl, pentyl, hexyl, and isomers thereof. Illustrative of included isomers are isopropyl, tert. butyl, neopentyl, 2,3-dimethylbutyl. Limitations of a different carbon number are interpreted in the same manner. For example, "alkyl of seven to 12 carbon atoms, inclusive" includes heptyl, octyl, nonyl, decyl, undecyl, dodecyl, and isomers thereof. Illustrative of included isomers are isoheptyl, 2,2,4-trimethylpentyl, 3,5-dimethylheptyl, 4-ethyloctyl, 2,3-diethylheptyl, and isododecyl. "Alkyl of one to 12 carbon atoms" includes the alkyls within the one to six and seven to 12 carbon atom range.

The phrase "a physiologically acceptable metal or amine cation" is that metal or amine which is accepted in a non-toxic manner by a mammal. Illustrative examples of such metals are the alkali metals, e.g., lithium, sodium and potassium, and the alkaline earth metals, e.g., magnesium and calcium. Other metals, e.g., aluminum, zinc, and iron are also within the scope of this invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about eighteen carbon atoms, as well as heterocyclic amines, e.g., piperidine, morpholine, pyrrolidine, piperazine, and lower-alkyl derivatives thereof, e.g., 1-methyl piperidine, 4-ethylmorpholine, 1-isopropylpyrrolidine, 2-methylpyrrolidine, 1,4-dimethylpiperazine, 2-methylpiperidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tertamylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium and the like.

The compounds of the invention can be prepared by methods known to the art. For example, methods outlined in U.S. Pat No. 3,639,249, Column 3, line 38 to Column 5, line 18, can be used with facility. W, X, Y and Z substituted meta or para diaminophenylene compounds are suitable starting materials. These compounds are reacted wtih an $R_1$ substituted oxalylhalide, with the proviso that $R_1$ is not hydrogen or a physiologically acceptable metal or amine cation, preferably the chloride in a suitable solvent and base to form a dioxamate of FIG. I. The ester can then be transesterified with known reagents and conditions to form a different ester. If less than stoichiometric quantities are employed in the transesterification, esters where $R_1$ and $R_2$ differ are readily prepared. After formation of the ester, less than stoichiometric quantities of reagents can be employed to prepare the half acid and the half metal or amine salt — the other half of the molecule being different but within the scope of $R_1$ and $R_2$.

The appropriate W, X, Y and Z substituted 3- or 4-amino aniline starting materials are prepared by conventional methods. Depending upon the substituent itself, the placement of the substituent and the placement of the oxamic group, the substitution of the benzene ring can occur on the benzene itself, or nitrobenzene, nitroaniline, dinitrobenzene, aminoaniline or combinations of these methods. Reduction of nitro to an amino grouping can be easily effected by catalytic means such as Raney Nickel, palladium on charcoal or platinum in the presence of hydrogen. Additionally, chemical means are also available for reduction of nitro to amino, for example, stannous chloride in concentrated hydrochloric acid and iron in acetic acid with ethanol.

The particular

substituents are prepared by converting the corresponding diamino or dinitro benzoic acid, for example, to the ester, amide, etc., by standard methods. This can be done prior to the preparation of the dioxamate from the substituted diamino starting material.

Once the substituted aniline starting material is prepared, it is reacted with an alkyl oxalyl halide or dialkyl oxalate. When using an alkyl oxalyl halide, reaction is carried out in base and solvent at standard conditions. Examples of suitable solvents are dimethylformamide, dioxane, and tetrahydrofuran. Appropriate bases include triethylamine, N-methylmorpholine, dimethylpiperazine, and N-methylpiperidine. When the dialkyl oxalate is employed, the starting material or its substituted analogue is heated together with the dialkyl oxalate or an additional solvent such as a xylene or diphenyl ester if desired, thereby forming the dioxamate. The temperature is from about 25°C. to the reflux temperature of the system.

The W, X, Y and Z substituted dioxamic compounds of this invention are illustratively exemplified in Tables I and II of U.S. patent application Ser. No. 382,762, filed July 26, 1973. The compounds of Table VII relating to Table I are also intended to be included within this case. These tables appear at Page 12, line 1, to Page 21, line 6, and Page 22, lines 4–7, and are incorporated within this application by reference. However, all those compounds which do not meet the overall proviso of the claim language are meant to be excluded from the claim language. Examples of such compounds are compounds where

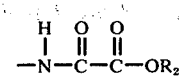

is at the 4 position and W, X, Y, and Z are all alkyl, all halogen, or all alkoxy, and combinations of such groups, for example, W and X are hydrogen, Y is chloro, Z is ethyl; W is hydrogen, X is chloro, Y is methoxy, and Z is propyl. Where

is at the 3 position, the 4-alkoxy, 4-alkyl and 4-halogen are not included within this invention, as previously disclosed.

Each of the compounds illustratively listed above are converted to a dioxamate of FIG. I where $R_1$ and $R_2$ are the same, with $R_1$ illustratively exemplified by the following:

TABLE I $R_1 = R_2$
$CH_3$
$C_3H_7$
$tC_4H_9$
$C_6H_{13}$
$iC_8H_{17}$
2,4-diethylpentyl
i-decyl
dodecyl
cyclobutyl
cyclopentyl
cyclohexyl
cycloheptyl
cyclooctyl
phenyl
benzyl
phenethyl
α,α-dimethylbenzyl
4-(phenyl)butyl
α,α-dimethylphenethyl
p-chlorophenyl
o-isopropylbenzyl m-pentylphenethyl
3-(p-isohexylphenyl)propyl
4-(o-isopropoxyphenyl)butyl
m-methoxyphenethyl
p-butoxyphenyl
m-phenylbenzyl
3-(o-fluorophenyl)propyl
m-bromophenethyl
p-(trifluoromethyl)phenyl
m-hydroxyphenethyl
o-aminobenzyl
m-nitrophenyl
p-carboxyphenethyl
m-cyano-$\alpha,\alpha$-dimethylbenzyl
4-(o-cyanophenyl)butyl
o-(methylamino)phenyl
m-(diethylamino)benzyl
p-(dibutylamino)phenethyl
o-(ethylmethylamino)-$\alpha,\alpha$-dimethylbenzyl
4-[m-(propylamino)phenyl]butyl
2-aminoethyl
3-(methylamino)propyl
4-(ethylamino)butyl
2-(methylpropylamino)ethyl
1-(butylethylamino)-1-methylethyl
2-(1-azetidinyl)ethyl
3-(1-pyrrolidinyl)propyl
4-(hexahydro-1H-azepin-1-yl)butyl

TABLE II

The compounds of Table I are converted to unsymmetrical esters ($R_1 \neq R_2$) by standard means.

TABLE III

The compounds of Tables I and II are converted by standard means to half esters when ether $R_1$ or $R_2$ is hydrogen or a physiologically acceptable metal or amine cation.

The following examples are compounds in accordance with this invention. The compounds are not intended to limit but merely to exemplify the invention.

EXAMPLE 1

Dibutyl N,N'-(2-chloro-5-cyano-m-phenylene)dioxamate a. n-Butyl oxalyl chloride

To 100 g. (0.79 mole) of stirred oxalyl chloride is added dropwise over the course of ½ hour 22.24 g. of n-butanol. The mixture is heated under reflux for 3 hours. The excess oxalyl chloride is removed by distillation and the residue distilled through a 6-inch helices-packed column in vacuo. There is obtained 39.3 g. (80%) of a colorless oil boiling at 64° (13 mm). This material is used directly as an intermediate in the following reaction.

b. Dibutyl N,N'-(2-chloro-5-cyano-m-phenylene)dioxamate

A solution of 5.70 g. (0.034 mole) of 4-chloro-3,5-diaminobenzonitrile, 16 mls. of dry dimethylformamide, and 8.30 g. (0.082 mole) of triethylamine is cooled to below 5° in an ice-bath. n-Butyl oxalylchloride (13.50 g. 0.082 mole) is added slowly to the stirred reaction mixture, attempting to keep the temperature below 15°. The mixture is stirred in an ice-bath for 1 hour and then allowed to warm to room temperature. After stirring at room temperature for 23 hours, the reaction mixture is poured into approximately 300 mls. of $H_2O$. This mixture is vigorously stirred for 5 to 10 minutes, yielding a semi-solid precipitate that is isolated by filtration. This semi-solid is recrystallized from benzene/hexane in two batches to give a total of 10.1 g. (52%) of brown needles, m.p. 118°–120°, 117°–118°. Two more recrystallizations of the lower melting batch raises its melting point to 120.0°–120.5°.

Analysis Calcd. for: $C_{19}H_{22}N_3O_6Cl$: C, 53.84; H, 5.23; Cl, 8.36; N, 9.91; Found: C, 53.89; H, 5.13; Cl 8.29; N, 9.94.

Infrared: (nujol) 3370, 3340 (NH) 3110 (=CH) 2240 (C ≡ N) 1725 (C=O) 1590, 1560, 1510 (C=C/amide 11) 1435 (CH) 1315, 1280, 1245, 1180, 1040 (C-O/C-N/other) $cm^{-1}$.

NMR: ($CDCl_3$): $\delta$11.30 (S,2,NH), $\delta$10,37 (S,2,aromatic), $\delta$4.47 (t, 4, $CH_2C_3H_7$), $\delta$2.23–0.63 (m,14, $CH_2C_3H_7$)

EXAMPLE 2

Dihexyl N,N'-(2-chloro-5-cyano-m-phenylene)-dioxamate a. n-Hexyl oxalyl chloride To 100 g. of stirred oxalyl chloride is added dropwise, 30.4 g. (0.3 mole) of n-hexanol. The mixture is then heated under reflux for three hours. The excess oxalyl chloride is removed by distillation under reduced pressure and the residue distilled through a 3 inch Vigreux Column. There is obtained 47.4 g. (82%) of a colorless liquid boiling at 93° (13 mm). This material is used directly in the following reaction.

b. Dihexyl N,N'-(2-chloro-5-cyano-m-phenylene)-dioxamate

A solution containing 5.70 g. (0.034 mole) of 4-chloro-3,5-diaminobenzonitrile, 16 mls. of dry dimethylformamide, and 8.30 g. (0.082 mole) of triethylamine is cooled to below 5° in an ice bath. n-hexyl oxalylchloride 15.79 g. (0.082 mole) is added slowly to the stirred mixture, attempting to keep the temperature below 15°. The reaction flask is then equipped with a drying tube and stirred for 1 hour in the ice-bath. The ice bath is then removed and the mixture stirred for 24 hours at room temperature. The mixture is poured into 300 mls. of $H_2O$ and with vigorous stirring a brown semi-solid mass forms. This solid is collected by filtration and dissolved in ethyl acetate and transferred to a round-bottomed flask. This solvent is evaporated on a rotary evaporator. Benzene is added to and evaporated from the flask several times to remove any $H_2O$ present. The product is placed in the refrigerator where it solidifies overnight. TLC of the product on silica gel using 10% methanol in benzene indicates that the product is a mixture with one major component. The product is placed at the top of a 500 g. silica gel column and the column eluted with benzene. Those fractions collected from the column containing the major component of the product mixture are combined and the solvent evaporated. Recrystallization of the residue from hexane yields 4.64 g. (28%) of white, waxy flakes melting at 82°–84°. Two more recrystallizations from hexane raises the melting point to 83.3°–84.5°.

Analysis Calcd. for: $C_{23}H_{30}ClN_3O_6$:
C, 57.56; H, 6.30; Cl, 7.39; N, 8.75;
Found: C, 57.80; H, 6.43; Cl, 7.52; N, 9.03

Infrared: (nujol mull) 3350 (NH) 3100 (NH/=CH) 2240 (C ≡ N) 1725, 1710 (C=O) 1585, 1550, 1510 (C=C/amide II) 1435, 1315, 1280, 1250, 1180 (CH/C-H/C-O) $cm^{-1}$.

NMR: (CDCl$_3$): δ10.87 (S, 2, NH), δ9.96 (S, 2, aromatic), δ4.43 (t, 4, CH$_2$C$_5$H$_{11}$), δ2.40–0.43 (m, 22, C$_5$H$_{11}$).

EXAMPLE 3

Hexyl N,N'-(2-Chloro-5-cyano-m-phenylene)-dioxamate, mono potassium salt

A suspension of dihexyl N,N'-(2-chloro-5-cyano-m-phenylene)dioxamate is stirred with one equivalent of anhydrous potassium acetate at reflux in aqueous solution for 4 hours. The mixture is filtered hot to remove unreacted dihexyl, N,N'-(2-chloro-5-cyano-m-phenylene)dioxamate and the aqueous filtrate is concentrated until the mixture is slightly turbid. After cooling in the refrigerator, the mixture is filtered. There is thus obtained the mono-potassium salt of hexyl N,N'-(2-chloro-5-cyano-m-phenylene)dioxamate.

EXAMPLE 4

Dibenzyl-N,N'-(2-chloro-5-cyano-m-phenylene)-dioxamate a. Benzyl oxalyl chloride A mixture of 90 g. (1 mole) of oxalic acid, 400 ml. of benzene and 108 g. (1 mole) of benzyl alcohol is stirred together and three drops of concentrated sulfuric acid are added. A Dean-Stark trap is placed on the apparatus and the mixture refluxed for 2 hours. The theoretical amount of water is obtained. One-half the volume of benzene is removed by distillation. The mixture is filtered while hot and the filtrate cooled to room temperature. The insoluble material is oxalic acid and weighs 45 g.

The cooled filtrate is stirred at room temperature and there is added 261.8 g. (2.2 moles) of thionyl chloride. The solution is refluxed for 3 hours. The benzene is removed by distillation. The oily residue is distilled through a 3 inch Vigreux Column. There is obtained a small amount of forerun that distills at 100°–112° at 20 mm. The remaining oil is distilled under high vacuum. There is obtained 40.6 g. of a clear colorless oil boiling at 95°–98° at 0.150 mm. The infrared spectra is in agreement for the expected compound.

b. Dibenzyl oxalate

A suspension of 90 g. (1.0 mole) of anhydrous oxalic acid in 224 g. (ca. 2.02 moles) of benzyl alcohol and 400 ml. of benzene is stirred while 0.25 g. of concentrated H$_2$SO$_4$ are added. The mixture is refluxed with stirring for about four hours using a Dean-Stark water trap to remove the H$_2$O formed. About 38 ml. of H$_2$O is collected. About 210 ml. of benzene is removed by distillation. The resulting concentrated benzene solution yields a silvery precipitate on cooling to room temperature overnight. The precipitate is filtered, washed with benzene and dried in vacuo. Wt.=118.6 g. M.P.=83–84°. An additional 42.5 g. of dibenzyl oxalate is recovered from the filtrate and washes. Total yield=161.1 g. (ca. 60%).

c. Monobenzyl oxalate, potassium salt

Dibenzyl oxalate (54.0 g., 0.2 mole) is suspended in 200 ml. of water containing 19.6 g. (0.2 mole) of potassium acetate (anhydrous). The mixture is rapidly heated to reflux with very efficient stirring so that the liquified dibenzyl oxalate is thoroughly emulsified in the refluxing aqueous layer. The refluxing and rapid stirring is continued for 4 hours. The mixture is cooled without agitation for about 45 minutes. At this time the initial oily lower layer has set to a solid cake. The clear supernatant liquid is decanted and refrigerated. The monobenzyl oxalate potassium salt which has crystallized overnight is filtered, washed with three small portions of ice water and dried in vacuo. Wt.=10.06 g. M.P. =247°(dec.) The filtrate and wash, on concentration to a solid in vacuo and recrystallization from 25 ml. of hot water, yields an additional 10.02 g. of the desired monopotassium salt.

Analysis Calcd. for: C$_9$H$_7$O$_4$K: C, 49.51; H, 3.23; Found: C, 49.65; H, 3.13.

d. Monobenzyl oxalyl chloride

A suspension of 40.1 g. (0.184 mole) of potassium monobenzyloxalate in 130 ml. of benzene is stirred thoroughly while 24.2 g. (0.204 mole) of SOCl$_2$ is added dropwise during 15 minutes. The mixture is cautiously heated to reflux to avoid excess foaming of the viscous material. The mixture is refluxed about two and one-half hours until the K salt is dissolved and a gelatinous mixture containing KCl is present. The KCl is filtered, washed with benzene, and the filtrate evaporated to a syrupy residue. Distillation of the residue in vacuo gives 32.78 g. (90%) of material boiling at 60°–61° (0.05 mm.).

e. Dibenzyl N,N'-(2-chloro-5-cyano-m-phenylene)-dioxamate

A solution of 1.17 g. (0.007 mole) of 4-chloro-3,5-diaminobenzonitrile in 5 ml. of dimethylformamide and 25 ml. of ethyl acetate is stirred and 1.68 g. (0.0166 mole) of triethylamine is added. The solution is stirred and there is added 3.30 g. (0.0166 mole) of benzyl oxalyl chloride in 10 ml. of dry ethylacetate. The mixture is stirred at room temperature and allowed to stand overnight.

The precipitate is removed by filtration and the filtrate evaporated to an oil in vacuo. The oil is poured into 100 ml. of water and triturated for thirty minutes. The water is removed by decantation and the solid recrystallized from ethanol. There is obtained 1.95 g. (57%) of cream colored needles melting at 108°–110°.

Analysis Calcd. for: C$_{25}$H$_{18}$N$_3$ClO$_6$: C, 61.04; H, 3.69; Cl, 7.21; N, 8.54; Found: C, 61.19; H, 3.99; Cl, 7.29; N, 8.36.

The infrared and NMR spectra are in agreement with the proposed structure.

EXAMPLE 5

Benzyl N,N'-(2-chloro-5-cyano-m-phenylene)-dioxamate, mono THAM salt

A suspension of dibenzyl N,N'-(2-chloro-5-cyano-m-phenylene)dioxamate in water is treated with one equivalent of tris(hydroxymethyl) aminomethane. The suspension is stirred at room temperature until most of the solid has dissolved. The mixture is filtered and the filtrate concentrated in vacuo at room temperature. The residue is dissolved in a small amount of water and anhydrous ethanol is added at the reflux point until the solution is slightly turbid. Upon standing in the refrigerator the solution precipitates as a solid. The material is removed by filtration and washed with a small amount of ethanol.

EXAMPLE 6

Diphenethyl N,N'-(2-chloro-5-cyano-m-phenylene)dioxamate a. Phenethyl oxalyl chloride A solution of 100 g. of oxalyl chloride is added dropwise to 36.65 g. (0.3 mole) of phenethyl alcohol with stirring. The solution is refluxed for three hours and the excess oxalyl chloride removed by distillation. The residue is distilled through a 6 inch helicespacked column. There is obtained 54 g. (85%) of a colorless oil boiling at 105° at 0.25 mm.

The infrared spectra is in agreement with the proposed structure.

b. Diphenethyl N,N'-(2-chloro-5-cyano-m-phenylene)dioxamate

A solution of 5.03 g. (0.03 mole) of 4-chloro-3,5-diaminobenzonitrile in 25 ml. of dry dimethylformamide and 180 ml. of ethyl acetate is stirred at room temperature. There is added 7.29 g. (0.072 mole) of triethylamine to the solution with continued stirring. To the stirred solution there is added slowly 15.31 g. (0.072 mole) of phenethyl oxalyl chloride. The mixture is stirred at room temperature for 2½ hours and allowed to stand overnight.

The precipitate is filtered and the filtrate evaporated to dryness in vacuo. The oily residue is poured into 400 ml. of water and stirred for fifteen minutes. The water is decanted and the residue recrystallized from ethanol. There is obtained 11 g. (71%) of yellow platelets melting at 116°–117°. Recrystallization of 1 g. of product gives 850 mg. of material melting at 119°–120°.

Analysis Calcd. for: $C_{27}H_{22}ClN_3O_6$: C, 62.37; H, 4.27; Cl, 6.82; N, 8.08; Found: C, 62.00; H, 4.28; Cl, 6.85; N, 8.05.

EXAMPLE 7

Diethyl N,N'-(2-chloro-5-phenyl-m-phenylene)dioxamate a. 2-Chloro-5-phenyl-m-phenylenediamine A solution of 2.79 g. (0.01 mole) of 4-chloro-3,5-dinitrobiphenyl [R. C. Hall and C. S. Giam, J. Agr. Food Chem. 20 (3) 546-52 (1972)] in 200 ml. of dioxane is hydrogenated at 3 atmospheres using Raney Nickel Catalyst. The catalyst is removed by filtration and the residue concentrated under reduced pressure. The residue is recrystallized from ethanol-water. There is obtained 1.12 g. (51%) of material melting at 142°–144.5°. Additional recrystallization raises the melting point to 146°–7°.

Analysis Calcd. for: $C_{12}H_{11}ClN_2$: C, 65.91; H, 5.07; Cl, 16.21; N, 12.81; Found: C, 65.75; H, 5.26; Cl, 15.52; N, 12.76.

b. Diethyl N,N'-(2-chloro-5-phenyl-m-phenylene)-dioxamate

To a stirred solution of 7.45 g. (0.034 moles) of 2-chloro-5-phenyl-m-phenylene diamine in 16 ml. of dry ethyl acetate and 8.30 g. (0.082 moles of triethylamine, cooled below 5° is added, dropwise, 11.20 g. (0.082 moles) of ethyl oxalyl chloride. An additional 20 ml. of ethyl acetate is added, the mixture is stirred in the ice-bath for an additional hour and then overnight at room temperature.

The mixture is diluted to a volume of 200 ml. by the addition of ethyl acetate and the solid removed by filtration and washed with water. The ethyl acetate filtrate is concentrated to dryness to give additional material.

The solids are combined and recrystallized from ethanol. There is obtained 11.66 g. (78%) of long thin rose-colored needles melting at 204°–205°.

Analysis Calcd. for: $C_{20}H_{19}ClN_2O_6$: C, 57.36; H, 4.57; Cl, 8.46; N, 6.69; Found: C, 57.38; H, 4.52; Cl, 8.51; N, 6.73.

In the invention's greatest breadth, the overall proviso of Page 4, lines 7–21, is not applied to the pharmaceutical compositions of the compounds of FIG. 1 and the methods of using the compounds of FIG. 1 for prophylactic treatment of allergy of a reagin or nonreagin mediated nature. Consequently, those compounds which were deleted from Tables I, II, and VII of Ser. No. 382,762 because they were within the overall proviso of the compound claim are within the broad concept of the pharmaceutical compositions and methods of using them. The compounds of Tables I, II, and VII which were deleted because of the overall proviso are incorporated by reference.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of FIG. 1. The preferred method of administration is by inhalation into the lung by means of an aerosol liquid or powder for insufflation, or orally.

For oral administration, either solid or fluid unit dosage forms can be prepared. For preparing solid compositions such as tablets, the compound of FIG. 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung. For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dispersing a compound of the FIG. I in water or ethanol and mixing with a volatile propellant and placing in a pressurized container having a metering valve to release a predetermined amount of material.

The liquefied propellant employed is one which has a boiling point below 65°F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.001 to about 20 mg. of compound in a single dose, administered parenterally or by inhalation in the compositions of this invention, are effective for preventing allergy attacks. More specifically, the single dose is from about 0.1 to about 5.0 mg. of compound. The oral and rectal dose is from about 0.1 to about 250 mg. in a single dose. More specifically, the single dose is from about 1.0 to about 100 mg. of compound. The dosage to be administered can be repeated up to four times daily.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto- immune diseases, exercise induced asthma, stress induced asthma, systemic anaphylaxis, and bird fancier's disease.

EXAMPLE 8

A lot of 10,000 tablets, each containing 1 mg. of dibenzyl N,N'-(2-chloro-5-cyano-m-phenylene)dioxamate is prepared from the following types and amounts of ingredients:

| | |
|---|---|
| Dibenzyl N,N'-(2-chloro-5-cyano-m-phenylene)dioxamate, micronized | 10 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever or asthma attacks at a dose of one tablet every 6 hours.

EXAMPLE 9

One thousand tablets, each containing 5 mg. of Dibenzyl N,N'-(2-chloro-5-cyano-m-phenylene)dioxamate are prepared from the following types and amounts of ingredients:

| | |
|---|---|
| Dibenzyl N,N'-(2-chloro-5-cyano-m-phenylene)dioxamate | 5 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food-allergy at a dose of one tablet before meals.

EXAMPLE 10

A sterile preparation suitable for intramuscular injection and containing 0.5 mg. of dibenzyl N,N'-(2-chloro-5-cyano-m-phenylene)dioxamate in each milliliter is prepared from the following ingredients:

| | |
|---|---|
| Dibenzyl N,N'-(2-chloro-5-cyano-m-phenylene)dioxamate micronized | 0.5 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected for prophylactic treatment of allergic rhinitis.

EXAMPLE 11

Six hundred ml. of an aqueous suspension containing 5.0 mg. of the dibenzyl N,N'-(2-chloro-5-cyano-m-phenylene)dioxamate per ml. is prepared as follows:

| | |
|---|---|
| Dibenzyl N,N'-(2-chloro-5-cyano-m-phenylene)dioxamate | 3.0 Gm. |
| Sodium chloride | 5 Gm. |
| Water for injection q.s. | 600 ml. |

The dibenzyl N,N'-(2-chloro-5-cyano-m-phenylene)-dioxamate and sodium chloride are dispersed in sufficient water to make 600 ml. and sterilized.

The liquid is placed in nebulizers designed to deliver 0.25 ml. per spray.

The liquid is inhaled into the lungs every 4 to 6 hours for prevention of asthmatic attacks.

EXAMPLE 12

A powder mixture consisting of 0.1 gram of dibenzyl N,N'-(2-chloro-5-cyano-m-phenylene)dioxamate and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 13

A powder mixture consisting of 0.1 gram of diphenethyl N,N'(2-chloro-5-cyano-m-phenylene)dioxamate and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 14

Twelve grams of an aerosol composition are prepared from the following ingredients:

| | |
|---|---|
| Dibenzyl N,N'-(2-chloro-5-cyano-m-phenylene)dioxamate, micronized | 0.012 Gm. |
| Freon 12 | 1.440 Gm. |
| Freon 114 | 2.160 Gm. |
| Water | 7.788 Gm. |
| Sorbitan monoleate | 0.600 Gm. |

The compound is dispersed in the water and chilled to $-30°C$. and added to the chilled Freons. The twelve grams of compositions are added to a 13 ml. plastic coated bottle and capped with a metering valve. The metering valve releases 80 mg. of composition in an aerosol. The aerosol is inhaled every 4 to 6 hours for prevention of asthmatic attacks.

EXAMPLE 15

After allowing for the differeing solubilities of the compounds and the activity of the particular compound as measured, for example, by the in vivo rat passive cutaneous anaphylaxis assay, a suitable quantity of each of the compounds of Table I through Table III and Examples 1–7, is substituted for the active compound in the compositions and uses of Examples 8 through 14. Results showing anti-allergy activity are obtained.

It should be noted that in all the compositions and treatment examples of this patent application, the quantity of drug employed refers to the acid equivalent.

EXAMPLE 16

The rat passive cutaneous anaphylaxis assay is run in the following manner:

Female Sprague-Dawley 250 gm. rats are skinsensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA) + 5 mg. Evans blue dye. The test compound is given by the oral route suspended in 0.25% methylcellulose. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

The inhibitory dose$_{50}$ for the dibenzyl N,N'-(2-chloro-5-cyano-m-phenylene)dioxamate is 0.5–1.0 mg./kg. by the oral route.

A further subgenus of this invention is where W and X are hydrogen,

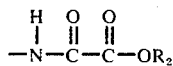

is located at the 3 position, Y is 5-acetyl, Z is at the 2 position and is selected from the group consisting of hydrogen, chloro, bromo, fluoro, alkyl of one to three carbon atoms, inclusive, and alkoxy of one to three carbon atoms, inclusive. $R_1$ and $R_2$ have the same scoping as in Group I.

It is also intended to incorporate, by reference, the compounds of Examples 3–18 of Ser. No. 382,762 appearing at Page 24, line 9, to Page 53, line 16. $R_1$ and $R_2$ have the general scoping of Group I compounds. Only those compounds not within the overall exclusion are included as compounds of the invention.

When repeated administration is desired, the compounds of this application which have a relatively short duration of activity can be administered in a priming dose-maintenance dose regimen as described in U.S. Ser. No. 382,762 at Page 58, line 19, to Page 59, line 9.

We claim:

1. A compound of the formula

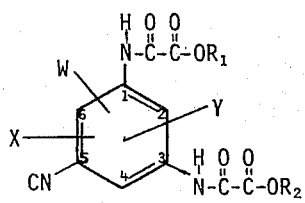

wherein W, X and Y are the same or different and are selected from the group consisting of hydrogen, alkyl from one to six carbon atoms, inclusive, phenyl, alkoxy with the alkyl group having from one to six carbon atoms, inclusive, hydroxy, nitro, halogen, trifluoromethyl and

wherein Q is selected from

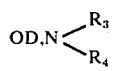

and

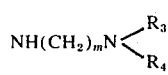

wherein D is selected from the group consisting of hydrogen, alkyl from one to six carbon atoms, inclusive, phenyl,

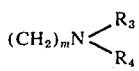

and a physiologically acceptable metal or amine cation, $m$ is 2 or 3. $R_3$ and $R_4$ are the same or different and are selected from the group consisting of hydrogen, alkyl from one to three carbon atoms, inclusive, $R_1$ and $R_2$ are the same or different and are selected from the group consisting of hydrogen, a physiologically acceptable metal or amine cation, alkyl of seven to twelve carbon atoms, inclusive, and cycloalkyl of four to eight carbon atoms, inclusive, with the proviso that when one of $R_1$ and $R_2$ is hydrogen or a physiologically acceptable metal or amine cation, the other variable is not hydrogen or a physiologically acceptable metal or amine cation.

2. A compound in accordance with claim 1 wherein W is hydrogen.

3. A compound in accordance with claim 2 wherein W and Y are hydrogen.

4. A compound in accordance with claim 3 wherein W, X and Y are hydrogen.

5. A compound in accordance with claim 2 wherein X and Y are the same or different and are selected from the group consisting of hydrogen, alkyl from one to six carbon atoms, inclusive, phenyl, alkoxy with the alkyl group having from one to six carbon atoms, inclusive, hydroxy, nitro, halogen, trifluoromethyl, and

with the proviso that when D is alkyl, the upper carbon atom limitation is three.

6. A compound in accordance with claim 5 wherein W and X are hydrogen.

7. A compound in accordance with claim 6 wherein Y is selected from the group consisting of hydrogen, alkyl of one to four carbon atoms, inclusive, phenyl, nitro, fluoro, chloro, trifluoromethyl and

$R_1$ and $R_2$ are the same or different and are selected from the group consisting of cycloalkyl of four to seven carbon atoms, inclusive.

8. A compound in accordance with claim 7 wherein Y is hydrogen.

9. A compound in accordance with claim 7 wherein Y is at the 2 position and is the same as in claim 7 with the proviso that

is limited to

and $R_1$ and $R_2$ are the same or different and are cycloalkyl of five or six carbon atoms.

10. A compound in accordance with claim 9 wherein Y is hydrogen.

11. A compound in accordance with claim 1 wherein $R_1$ is the same as $R_2$ and neither $R_1$ nor $R_2$ is hydrogen or a physiologically acceptable metal or amine cation.

12. A compound in accordance with claim 5 wherein $R_1$ is the same as $R_2$ and neither $R_1$ nor $R_2$ is hydrogen or a physiologically acceptable metal or amine cation.

13. A compound in accordance with claim 7 wherein $R_1$ is the same as $R_2$ and neither $R_1$ nor $R_2$ is hydrogen or a physiologically acceptable metal or amine cation.

14. A compound in accordance with claim 9 wherein $R_1$ is the same as $R_2$ and neither $R_1$ nor $R_2$ is hydrogen or a physiologically acceptable metal or amine cation.

15. A compound in accordance with claim 3 wherein X is hydrogen.

16. A compound in accordance with claim 3 wherein X is 2-chloro.

17. A compound in accordance with claim 3 wherein X is 4-chloro.

* * * * *